United States Patent
Safai et al.

(10) Patent No.: US 8,185,326 B2
(45) Date of Patent: May 22, 2012

(54) CORROSION DETECTION AND MONITORING SYSTEM

(75) Inventors: Morteza Safai, Seattle, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 516 days.

(21) Appl. No.: 12/390,983

(22) Filed: Feb. 23, 2009

(65) Prior Publication Data
US 2010/0217538 A1    Aug. 26, 2010

(51) Int. Cl.
*G01N 31/00*    (2006.01)

(52) U.S. Cl. ............... 702/30; 702/33; 702/34; 702/35; 702/36

(58) Field of Classification Search ............ 702/30, 702/33, 34, 35, 36
See application file for complete search history.

(56) References Cited

U.S. PATENT DOCUMENTS

| | | | |
|---|---|---|---|
| 5,043,784 A * | 8/1991 | Yamamoto et al. .......... 257/56 |
| 5,482,890 A | 1/1996 | Liu et al. |
| 6,379,622 B1 | 4/2002 | Polak et al. |
| 6,627,914 B1 | 9/2003 | Komiyama et al. |
| 6,657,232 B2 | 12/2003 | Morkoc |
| 6,717,664 B2 | 4/2004 | Floyd et al. |
| 7,002,079 B2 | 2/2006 | Mitchell et al. |
| 7,005,669 B1 | 2/2006 | Lee |
| 7,342,235 B1 | 3/2008 | Harrison et al. |
| 7,528,372 B2 | 5/2009 | Garvey et al. |
| 2003/0058506 A1 * | 3/2003 | Green et al. .............. 359/172 |
| 2003/0160182 A1 | 8/2003 | Petrich et al. |
| 2004/0211894 A1 | 10/2004 | Hother et al. |
| 2004/0241424 A1 | 12/2004 | Barbera-Guillem |
| 2004/0256612 A1 | 12/2004 | Mohseni et al. |
| 2005/0164169 A1 * | 7/2005 | Malak .......................... 435/5 |
| 2006/0152706 A1 | 7/2006 | Butland |
| 2007/0048867 A1 | 3/2007 | Farmer |
| 2007/0165215 A1 * | 7/2007 | Haridas ...................... 356/301 |
| 2007/0194297 A1 | 8/2007 | McCarthy et al. |
| 2007/0222880 A1 * | 9/2007 | Tafas .......................... 348/308 |
| 2008/0050513 A1 | 2/2008 | Wang et al. |
| 2008/0312847 A1 | 12/2008 | Safai et al. |

FOREIGN PATENT DOCUMENTS

| | | |
|---|---|---|
| EP | 2003439 A1 | 12/2008 |
| EP | 2221600 A1 | 8/2010 |
| WO | WO2005124340 A1 | 12/2005 |
| WO | WO2006107331 A1 | 10/2006 |
| WO | WO20061007493 A1 | 10/2006 |

OTHER PUBLICATIONS

U.S. Appl. No. 12/335,724, filed Dec. 16, 2008, Davis et al.
U.S. Appl. No. 12/390,965, filed Feb. 23, 2009, Safai et al.

(Continued)

*Primary Examiner* — Janet Suglo
(74) *Attorney, Agent, or Firm* — Yee & Associates, P.C.

(57) ABSTRACT

A method and apparatus comprises a number of sensors and a computer. The number of sensors is capable of being associated with a location of an object having quantum dots. The number of sensors is capable of sending energy into the location, and the energy is capable of causing a response from the quantum dots. The number of sensors is capable of detecting the response. The computer is coupled to the number of sensors and capable of determining whether corrosion is present in the location using the response detected by the number of sensors.

28 Claims, 9 Drawing Sheets

OTHER PUBLICATIONS

Bakkers et al., Excited-State Dynamics in CdS Quantum Dots Adsorbed on a Metal Electrode, J Phys Chem B, vol. 103, No. 14, 1999, pp. 2781-2788.

"Making Nanodots Useful for Chemistry" Jun. 19, 2003, 1 page http://www.sciencedaily.com/releases/2003/06/030619075658.htm.

USPTO office action for U.S. Appl. No. 12/390,965 dated Aug. 20, 2010.

European Search Report for European Patent Application No. 2221600 dated Mar. 31, 2010 (2 pages).

* cited by examiner

CORROSION DETECTION AND MONITORING SYSTEM

CROSS REFERENCE TO RELATED APPLICATION

The present disclosure is related to the following patent application entitled "Portable Corrosion Detection Apparatus", Ser. No. 12/390,965, issued as U.S. Pat. No. 7,902,524; filed even date hereof, assigned to the same assignee, and incorporated herein by reference.

BACKGROUND INFORMATION

1. Field

The present disclosure relates generally to inspecting objects and, in particular, to a method and apparatus for nondestructive inspection of objects. Still more particularly, the present disclosure relates to a method and apparatus for inspecting an object using quantum dots associated with the object.

2. Background

Ensuring that external and/or internal surfaces of an object do not have any corrosion may be important during the manufacture, maintenance, and/or rework of objects, such as aircraft, aircraft structures, and/or parts for aircraft. Locations for an aircraft in which corrosion detection may be desired include, for example, without limitation, a cargo bay, a door sill, a landing gear bay, an insulation blank, a bilge, a seat track, a leading edge of a wing, a trailing edge of a wing, a trailing edge of a stabilizer, a fuel tank, and/or other suitable locations.

Corrosion, however, on an object may be hidden and/or masked underneath layers of paint or other coatings. Destructive corrosion detection is one technique for detecting corrosion. This technique involves removing paint and/or disassembling parts and assemblies to determine whether corrosion is present. These processes are destructive, slow, inefficient, and/or may be cost prohibitive.

Another type of inspection is nondestructive inspection. This type of inspection may be used without destroying, damaging, and/or disassembling the object. Currently available nondestructive corrosion inspection is performed visually using electromagnetic inspection, eddy current, and/or ultrasonic inspection methods. Eddy current and ultrasonic inspection measure material loss. Early detection of corrosion may depend on the amount and nature of the material loss.

Visual inspections also may require a technician and/or other maintenance personnel to visually inspect all surfaces for signs of corrosion. These signs may include, for example, visible rust. However, visual inspections may miss corrosion in early stages. The technician and/or maintenance personnel may be unable to identify corrosion that may be present until the corrosion on a surface is substantial enough to be detected visually. Further, with the increasing complexity of aircraft structures and substructures, visual inspections may be more difficult without some disassembly.

These approaches may require more time, expense, inspections, and/or disassembly of the objects than would otherwise be desired for an early detection and monitoring capability.

Therefore, it would be advantageous to have an improved method, apparatus, and computer usable program code for nondestructive corrosion detection.

SUMMARY

In one advantageous embodiment, an apparatus comprises a number of sensors and a computer. The number of sensors is capable of being associated with a location of an object having quantum dots. The number of sensors is capable of sending energy into the location, and the energy is capable of causing a response from the quantum dots. The number of sensors is capable of detecting the response. The computer is coupled to the number of sensors and is capable of determining whether corrosion is present in the location using the response detected by the number of sensors.

In another advantageous embodiment, a sensor comprises a housing, a laser, a detector, and a transmitter. The housing is capable of being associated with a surface of an object having quantum dots. The laser is attached to the housing and is capable of transmitting a laser beam onto the surface of the object. The detector is attached to the housing and is capable of detecting a response to the laser beam generated by the quantum dots. The transmitter is capable of sending the response to a computer over a network.

In yet another advantageous embodiment, a method for detecting corrosion is present. Energy is sent into a location for an object from a number of sensors associated with the location. The location is associated with quantum dots. A response to the energy sent into the location from the number of sensors is detected. A determination is made as to whether the corrosion is present based on the response.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION

Figure 1:
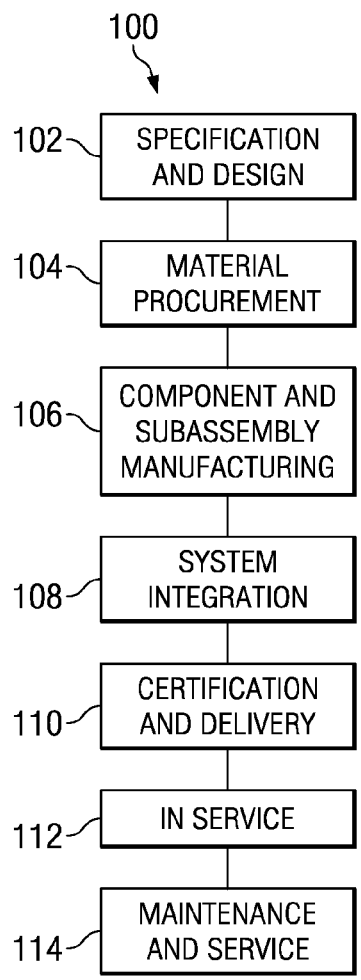
FIG. 1 is a diagram illustrating an aircraft manufacturing and service method in accordance with an advantageous embodiment.
Figure 2:
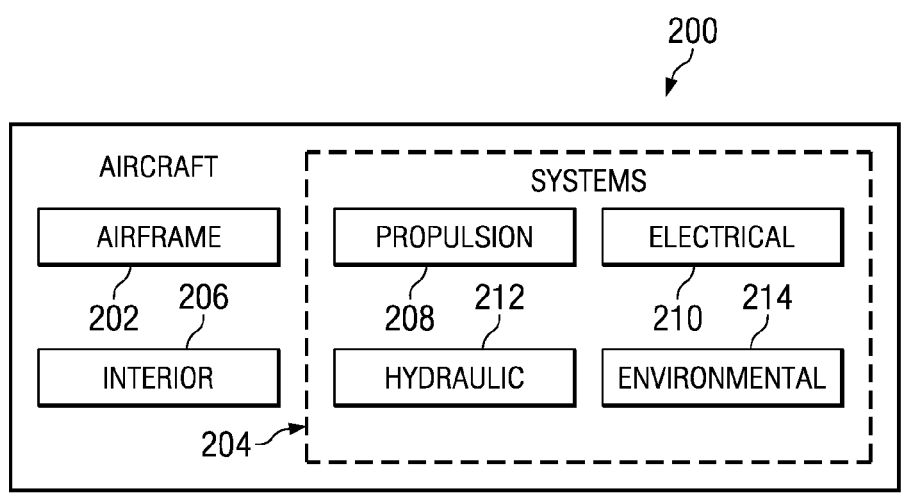
FIG. 2 is a diagram of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1. For example, a health monitoring system, in accordance with an advantageous embodiment, may be installed during component and subassembly manufacturing 106 and/or system integration 108. The health monitoring system may be used during in service 112 and/or during maintenance and service 114 to determine whether corrosion may be present in aircraft 200.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

One or more of the advantageous embodiments take into account and recognize that it would be desirable to have a method and apparatus to monitor for corrosion. The different advantageous embodiments also recognize and take into account that it would be desirable to have a method and apparatus for detecting corrosion that may be performed in a nondestructive manner. Further, the different advantageous embodiments recognize and take into account that it would be desirable to detect corrosion earlier than possible with currently available techniques.

The different advantageous embodiments provide a number of sensors capable of being associated with a location of an object having quantum dots. The number of sensors is capable of sending energy into the location and detecting a response to the energy. Further, a computer is coupled to the number of sensors. The computer is capable of determining whether corrosion is present in the location using the response detected by the number of sensors. A number of items, as used herein, refers to one or more items. For example, a number of sensors is one or more sensors.

Figure 3:
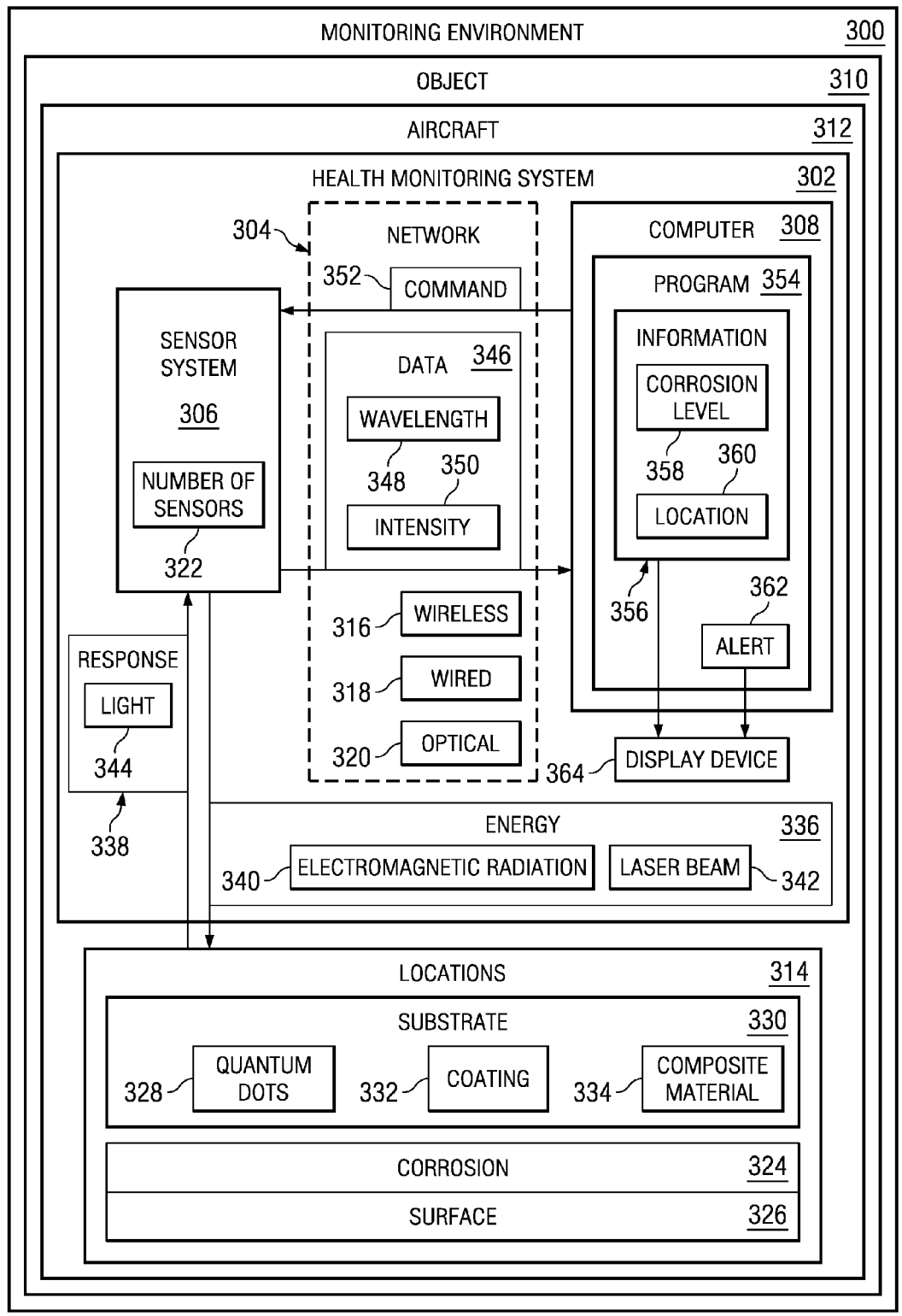
FIG. 3 is a diagram of a monitoring environment in accordance with an advantageous embodiment.

Turning now to FIG. 3, a diagram of a monitoring environment is depicted in accordance with an advantageous embodiment. Monitoring environment 300 is an example of an environment that may be implemented in an object such as, for example, without limitation, aircraft 200 in FIG. 2.

In this example, health monitoring system 302 is present in monitoring environment 300. Health monitoring system 302 may include network 304, sensor system 306, and computer 308. Health monitoring system 302 is associated with object 310. Health monitoring system 302 may be associated with object 310 by being attached to, integrated into, and/or otherwise associated with object 310.

In these examples, object 310 takes the form of aircraft 312, which may be, for example, aircraft 200 in FIG. 2. For example, sensor system 306 may be associated with locations 314 in aircraft 312. Computer 308 may be located in or remotely from aircraft 312, depending on the particular implementation.

Network 304 couples sensor system 306 to computer 308 in these examples. Network 304 provides a capability to provide communications between sensor system 306 and computer 308. In these examples, network 304 may take various forms. For example, network 304 may be wireless 316, wired 318, optical 320, and/or some other suitable type of network.

In the different advantageous embodiments, sensor system 306 may contain number of sensors 322. Number of sensors 322 may be associated with locations 314 in a manner to monitor for corrosion 324 on or around surface 326 of aircraft 312 in locations 314. Number of sensors 322 may be, for example, without limitation, attached to surface 326, secured to a structure around surface 326, and/or otherwise positioned to be capable of detecting corrosion 324 in locations 314.

In these illustrative examples, corrosion 324 may refer to a breaking down of properties in the material in an object due to chemical reactions with the surroundings around the object. For example, corrosion 324 may occur with a loss of electrons of metals. This loss may occur from a metal reacting with water and oxygen. This reaction forms free hydrogen+, H+. Corrosion 324 also may be a wearing and/or thickness in a material in the surface of an object; a crack, a fracture, and/or a break in the surface material of an object; and/or erosion in the material in the surface of the object.

Corrosion 324 may be caused by exposure to weather, heat, pressure, an impact, corrosive chemicals, rust, energy, light, an oxidation process, and/or exposure to any other corrosive substance or process that may result in destruction and/or wearing of a surface material and/or surface coating on an object. For example, a crack in paint may expose a substrate of a structure to moisture, which may result in corrosion 324.

Locations 314 may be critical areas and/or hot spots for corrosion 324. In other words, locations 314 may be locations in which corrosion 324 may likely occur. Of course, depending on the particular implementation, locations 314 may encompass all of aircraft 312.

In these different advantageous embodiments, the detection of corrosion 324 by health monitoring system 302 may be performed using quantum dots 328. Quantum dots 328 may be located on and/or in substrate 330 in locations 314. Substrate 330 may be, for example, coating 332 located on surface 326 in locations 314.

For example, without limitation, coating 332 may be paint, a polymer layer, or some other suitable type of material. In other advantageous embodiments, substrate 330 may be a part of object 310 in locations 314. For example, substrate 330 may take the form of composite material 334. Quantum dots 328 may be integrated into composite material 334. In yet other advantageous embodiments, quantum dots 328 may be attached to and/or bonded to surface 326 of aircraft 312. Surface 326 may include external and/or internal surfaces. For example, without limitation, surface 326 may include surfaces in internal structures of aircraft 312.

In these examples, a quantum dot is a semiconductor element whose excitations are confined in three-dimensional spatial dimensions. Quantum dots 328 are capable of being designed to emit a response after having been exposed to free electrons and/or free hydrogen+. The free hydrogen+ may be a hydrogen+ atom freed from a water molecule.

This response is light in these illustrative examples. For example, the response may be different after being exposed to free electrons as compared to prior to being exposed to free hydrogen+. For example, free hydrogen+ may be produced during a chemical reaction that causes corrosion 324. Further, in some advantageous embodiments, quantum dots 328 may provide a different response when exposed to air as opposed to when embedded in a material. In these different advantageous embodiments, quantum dots 328 may have a shape in the form of a sphere.

In these illustrative examples, number of sensors 322 in sensor system 306 may send energy 336 into surface 326 at locations 314. Response 338 is detected by number of sensors 322. In these examples, energy 336 takes the form of electromagnetic radiation 340. In particular, energy 336 may take the form of laser beam 342. Of course, energy 336 also may take other forms. For example, without limitation, energy 336 may be electricity, microwaves, heat, or other suitable types of energy.

Response 338 takes the form of light 344 in these illustrative examples. Light 344 may be visible and/or non-visible, depending on quantum dots 328.

Number of sensors 322 is capable of detecting light 344 in response 338. Number of sensors 322 may send data 346 to computer 308 in response to detecting response 338. Data 346 may include, for example, wavelength 348 and/or intensity 350 for light 344 as detected by number of sensors 322. Computer 308 may process data 346 to determine whether corrosion 324 is present.

In operation, number of sensors 322 may transmit energy 336 into locations 314 in response to various events. For example, energy 336 may be transmitted by number of sensors 322 in response to computer 308 sending command 352 to number of sensors 322. In yet other advantageous embodiments, number of sensors 322 may transmit energy 336 into locations 314 after a selected period of time has elapsed or in response to some other event.

Computer 308 may process data 346 using program 354, which executes on computer 308. Program 354 may perform an analysis of data 346 to determine whether corrosion 324 is present. Program 354 may generate information 356. Information 356 may include, for example, without limitation, corrosion level 358, location 360, and/or other suitable information. Further, program 354 also may generate alert 362. Alert 362 may indicate that maintenance, repair, and/or other actions may need to be taken. Information 356 and alert 362 may be presented on display device 364 in aircraft 312.

In this manner, health monitoring system 302 may be capable of monitoring aircraft 312 for corrosion 324 in locations 314 without requiring disassembly of aircraft 312. This capability may be provided by installing number of sensors 322 during the manufacture of aircraft 312. Further, number of sensors 322 may be installed after aircraft 312 has been manufactured. For example, number of sensors 322 may be installed during maintenance upgrades and/or other operations performed on aircraft 312.

Further, this monitoring may be performed while aircraft 312 is in service, during maintenance, or at any other suitable period of time. Health monitoring system 302 does not require maintenance personnel or other operators to travel to or visually inspect locations 314 in aircraft 312.

The illustration of FIG. 3 is not meant to imply physical or architectural limitations to the manner in which different advantageous embodiments may be implemented. In some advantageous embodiments, other components in addition to, or in place of, the ones illustrated may be employed. In yet other advantageous embodiments, some of the illustrated components may be unnecessary.

For example, additional sensors, in addition to number of sensors 322, may be placed in other locations other than locations 314 to monitor for corrosion in those locations. In still other advantageous embodiments, computer 308 may be unnecessary in health monitoring system 302, as associated with aircraft 312. For example, network 304 may transmit data 346 to a computer located in a location remote to aircraft 312. In yet other advantageous embodiments, other types of sensor systems may be used in addition to number of sensors 322 for detecting response 338 in response to transmission of energy 336. For example, other types of sensors such as, for example, ultrasonic sensors, also may be employed in addition to number of sensors 322.

Figure 4:
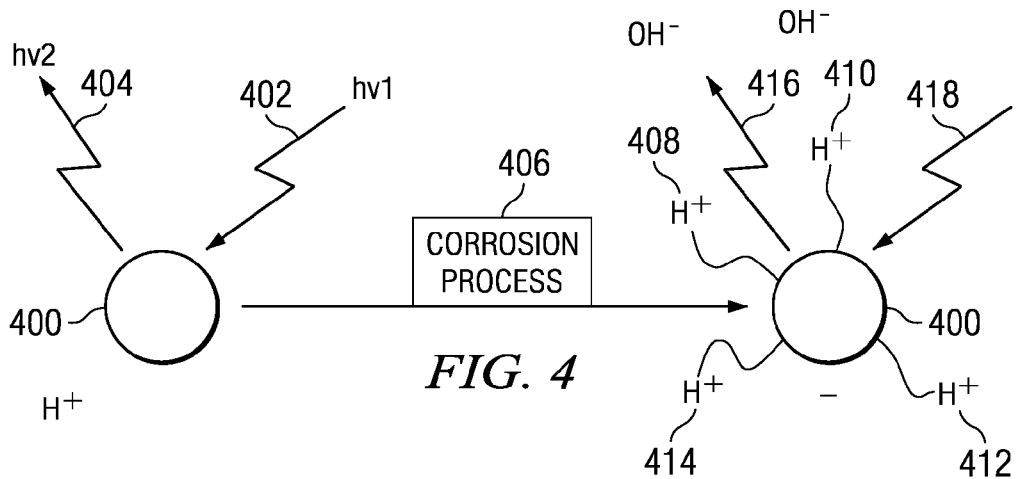
FIG. 4 is a diagram illustrating the responses generated by a quantum dot in accordance with an advantageous embodiment.

With reference now to FIG. 4, a diagram illustrating the responses generated by a quantum dot is depicted in accordance with an advantageous embodiment. In this example, quantum dot 400 is an example of a quantum dot in quantum dots 328 in FIG. 3.

Quantum dot 400 may receive energy 402 from an energy source such as, for example, without limitation, a laser beam. In response, quantum dot 400 may emit light 404. Light 404, emitted by quantum dot 400, has a wavelength and/or intensity when no corrosion is present.

When corrosion occurs, corrosion process 406 may expose quantum dot 400 to free hydrogen+, such as free hydrogen+ 408, 410, 412, and 414. This free hydrogen+ may occur from a reaction of water with the substrate. Corrosion process 406 may occur when moisture and/or some other fluid acting as an electrolyte comes into contact with an object in the aircraft. This contact may occur, for example, without limitation, through a scratch, an abraded area, and/or penetration of the paint and/or primer coating.

Exposure to free hydrogen+ 408, 410, 412, and 414 may result in free hydrogen+ 408, 410, 412, and 414 being attracted to and/or attached to quantum dot 400. This attachment causes quantum dot 400 to emit light 416 when exposed to energy 418. Light 416 may have a different wavelength and/or intensity as compared to light 404 because of exposure of quantum dot 400 to free hydrogen+ 408, 410, 412, and 414. Light 416 may have a different wavelength if one or more of free hydrogen+ 408, 410, 412, and/or 414 bond to quantum dot 400.

In these illustrative examples, the emission of light 416 may occur only when quantum dot 400 has free hydrogen+ 408, 410, 412, and 414 attached to quantum dot 400 and when energy 418 has a specific or selected wavelength. In other words, if energy 418 has a wavelength outside of the selected wavelength, quantum dot 400 may not generate light 416.

As a result, quantum dot 400 may only generate light 416 when energy 418 is applied to quantum dot 400 and free hydrogen+ 408, 410, 412, and 414 have become attached to quantum dot 400. In this illustrative example, four free hydrogen+ atoms are shown attached to quantum dot 400. Of course, the generation of light 416 may occur with other numbers of free hydrogen+ atoms are attached to quantum dot 400. For example, light 416 may be generated when one free hydrogen+ atom, two free hydrogen+ atoms, 18 free hydrogen+ atoms, or some other number of free hydrogen+ atoms are attached to quantum dot 400.

With the use of quantum dots, such as quantum dot 400, the detection of light 416, when corrosion process 406 has occurred, may provide a capability to measure very small amounts of corrosion caused by corrosion process 406. These small amounts of corrosion may be much smaller than the amounts of corrosion required for detecting a material loss that is used to produce the corrosion that is currently detectable by current processes.

Figure 5:
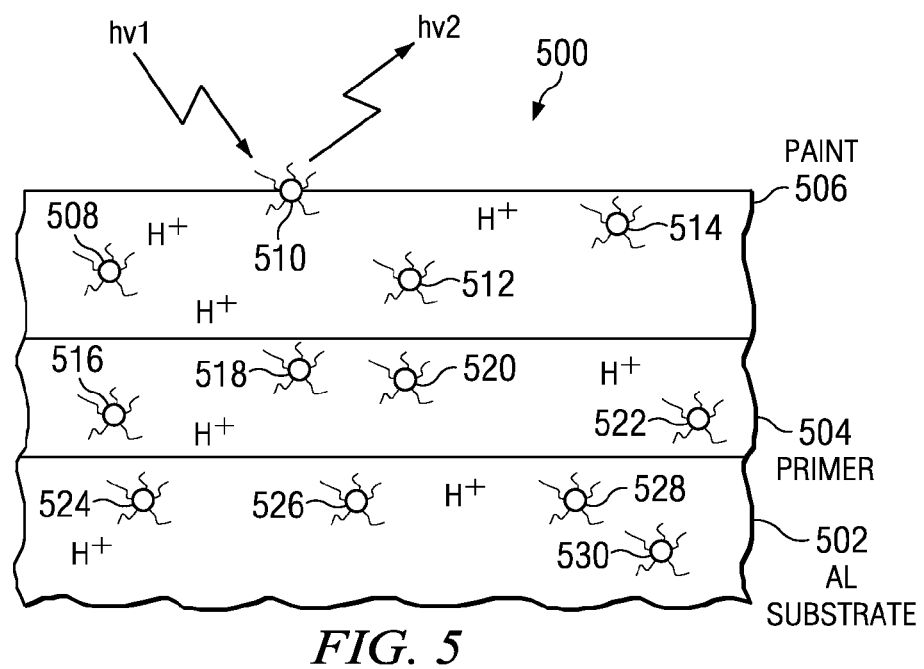
FIG. 5 is a diagram illustrating quantum dots in a location for an object in accordance with an advantageous embodiment.

Turning now to FIG. 5, a diagram illustrating quantum dots in a location for an object is depicted in accordance with an advantageous embodiment. In this example, a portion of object 500 is depicted in accordance with an advantageous embodiment. Object 500 is an example of a portion of object 310 in FIG. 3. In this illustrative example, object 500 includes substrate 502, primer layer 504, and paint layer 506.

In these examples, quantum dots may be present in at least one of substrate 502, primer layer 504, and paint layer 506. As used herein, the phrase "at least one of", when used with a list of items, means that different combinations of one or more of the items may be used and only one of each item in the list may be needed. For example, "at least one of item A, item B, and item C" may include, for example, without limitation, item A, or item A and item B. This example also may include item A, item B, and item C, or item B and item C.

In this illustrative example, quantum dots 508, 510, 512, and 514 are present in paint layer 506. Quantum dots 516, 518, 520, and 522 are present in primer layer 504. Quantum dots 524, 526, 628, and 530 are present within substrate 502. In the different advantageous embodiments, these quantum dots may be manufactured using any known and/or currently available process for manufacturing, producing, and/or otherwise generating quantum dots.

In this example, quantum dots are shown as being present in the different layers in object 500. Depending on the particular implementation, the quantum dots may be present in only one layer or some other combination of layers. Further, quantum dots also may be placed into a polymer coating specifically for use in corrosion detection.

The different advantageous embodiments recognize that quantum dots may be associated with object 500 in a number of different ways. As illustrated in these examples, quantum dots may be embedded directly into substrate 502.

Substrate 502 may be, for example, an aluminum substrate, a composite substrate, and/or some other suitable type of material. When used in primer layer 504 and/or paint layer 506, quantum dots may be prepared colloidally. In this manner, the quantum dots may be free floating and attached to various molecules via metal coordinating functional groups.

These groups include, but are not limited to, thiol, amine, nitrile, phosphine, phosphine oxide, phosphonic acid, carboxylic acid, and/or other ligands. This capability to attach to other molecules greatly increases the flexibility of quantum dots with respect to the types of environments in which they can be applied. By bonding appropriate molecules to the surface of a commodity, the quantum dots can be dispersed or dissolved in nearly any solvent or incorporated into a variety of inorganic and organic films. In addition, the surface chemistry can be used to effectively alter the properties of the quantum dots, including the brightness and electronic lifetimes of the quantum dots.

The different quantum dots may be selected to emit light in different wavelengths, resulting in different colors. This type of implementation may be used to identify the location of different quantum dots. For example, quantum dots in paint layer 506 may be selected to emit a different light color when exposed to free hydrogen+ as compared to quantum dots in primer layer 504, which may generate a different wavelength of light when exposed to free hydrogen+.

In other words, the wavelength of light emitted from a quantum dot may be related to the size and/or material used for a quantum dot. Quantum dots may be tunable, such that the signals or wavelengths emitted by a quantum dot can be selected and/or adjusted by changing the size of the quantum dot and/or changing the composition of the material in the quantum dot.

For example, the emission wavelength and, consequently, the color of light emitted by the quantum dot, can be altered simply by changing the size of the quantum dot. In these depicted examples, smaller quantum dots yield smaller or shorter wavelengths that tend to fall more within the blue color range of light. Larger quantum dots emit longer wavelengths of light, which produces a red-colored light emission.

Quantum dots of different sizes can be tethered and/or linked together to form molecules, attached to a polymer backbone, linked or tethered to form chains, and/or linked to form lattices. Each quantum dot in these chains and/or lattices that are of differing sizes will emit different wavelengths of light. In this manner, different sized quantum dots can be linked together to form lattices of quantum dots that will emit different colored lights in different patterns.

In other words, a grouping of quantum dots of different sizes and/or types may result in a pattern of light in which each of the quantum dots in the molecule emits light with a different wavelength. These different wavelengths, when emitted by the molecule, form the pattern for the molecule.

Further, multiple sized quantum dots may be mixed together and then linked. This mixture may result in a pattern being present in a response generated by the quantum dots. This response may be multi-colored and can be identified by a unique quantum dot pattern in a fashion similar to a barcode. Thus, a quantum dot barcode with specific fluoroscopic characteristics may be selectively or uniformly embedded into the material used to manufacture an object or into a coating applied to the object.

Figure 6:
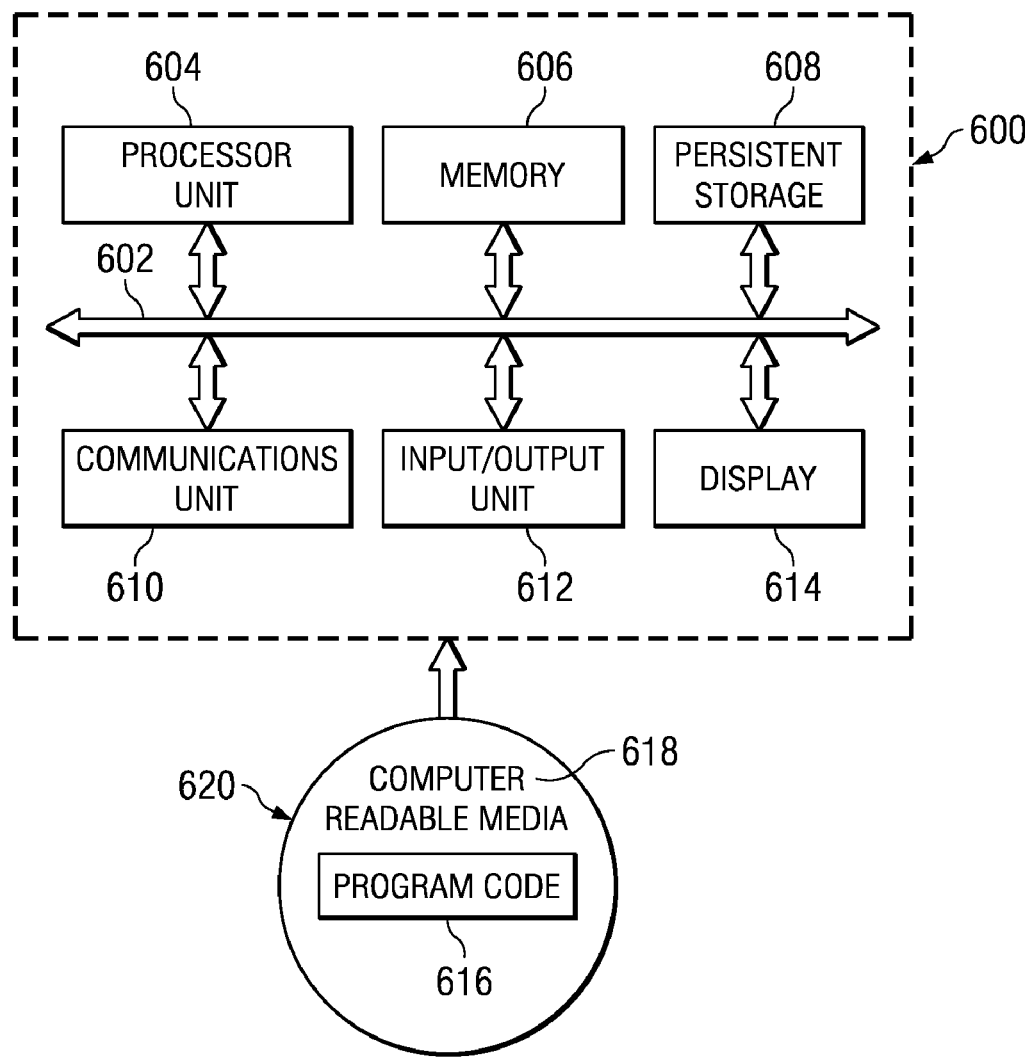
FIG. 6 is a diagram of a data processing system in accordance with an illustrative embodiment.

Turning now to FIG. 6, a diagram of a data processing system is depicted in accordance with an illustrative embodiment. Data processing system 600 is an example of a data processing system that may be used to implement computer 308 in health monitoring system 302 in FIG. 3. In this illustrative example, data processing system 600 includes communications fabric 602, which provides communications between processor unit 604, memory 606, persistent storage 608, communications unit 610, input/output (I/O) unit 612, and display 614.

Processor unit 604 serves to execute instructions for software that may be loaded into memory 606. Processor unit 604 may be a set of one or more processors or may be a multiprocessor core, depending on the particular implementation. Further, processor unit 604 may be implemented using one or more heterogeneous processor systems in which a main processor is present with secondary processors on a single chip. As another illustrative example, processor unit 604 may be a symmetric multi-processor system containing multiple processors of the same type.

Memory 606 and persistent storage 608 are examples of storage devices. A storage device is any piece of hardware that is capable of storing information either on a temporary basis and/or a permanent basis. Memory 606, in these examples, may be, for example, a random access memory or any other suitable volatile or non-volatile storage device.

Persistent storage 608 may take various forms, depending on the particular implementation. For example, persistent storage 608 may contain one or more components or devices. For example, persistent storage 608 may be a hard drive, a flash memory, a rewritable optical disk, a rewritable magnetic tape, or some combination of the above. The media used by persistent storage 608 also may be removable. For example, a removable hard drive may be used for persistent storage 608.

Communications unit 610, in these examples, provides for communications with other data processing systems or devices. Communications unit 610, in these examples, may provide a capability to couple data processing system 600 to sensors, such as number of sensors 322 in FIG. 3. This coupling may take the form of an exchange of data between these components over a network, such as network 304 in FIG. 3. In these examples, communications unit 610 is a network interface card. Communications unit 610 may provide communications through the use of either or both physical and wireless communications links.

Input/output unit 612 allows for input and output of data with other devices that may be connected to data processing system 600. For example, input/output unit 612 may provide a connection for user input through a keyboard and mouse. Further, input/output unit 612 may send output to a printer. Display 614 provides a mechanism to display information to a user.

Instructions for the operating system and applications or programs are located on persistent storage 608. These instructions may be loaded into memory 606 for execution by processor unit 604. The processes of the different embodiments may be performed by processor unit 604 using computer-implemented instructions, which may be located in a memory, such as memory 606.

These instructions are referred to as program code, computer usable program code, or computer readable program code that may be read and executed by a processor in processor unit 604. The program code in the different embodiments may be embodied on different physical or tangible computer readable media, such as memory 606 or persistent storage 608.

Program code 616 is located in a functional form on computer readable media 618 that is selectively removable and may be loaded onto or transferred to data processing system 600 for execution by processor unit 604. Program code 616 and computer readable media 618 form computer program product 620 in these examples. In one example, computer readable media 618 may be in a tangible form such as, for example, an optical or magnetic disk that is inserted or placed into a drive or other device that is part of persistent storage 608 for transfer onto a storage device, such as a hard drive, that is part of persistent storage 608.

In a tangible form, computer readable media 618 also may take the form of a persistent storage, such as a hard drive, a thumb drive, or a flash memory, that is connected to data processing system 600. The tangible form of computer readable media 618 is also referred to as computer recordable storage media. In some instances, computer readable media 618 may not be removable.

Alternatively, program code 616 may be transferred to data processing system 600 from computer readable media 618 through a communications link to communications unit 610 and/or through a connection to input/output unit 612. The communications link and/or the connection may be physical or wireless in the illustrative examples. The computer readable media also may take the form of non-tangible media, such as communications links or wireless transmissions containing the program code.

In some illustrative embodiments, program code 616 may be downloaded over a network to persistent storage 608 from another device or data processing system for use within data processing system 600. For instance, program code stored in a computer readable storage medium in a server data processing system may be downloaded over a network from the server to data processing system 600. The data processing system providing program code 616 may be a server computer, a client computer, or some other device capable of storing and transmitting program code 616.

The different components illustrated for data processing system 600 are not meant to provide architectural limitations to the manner in which different embodiments may be implemented. The different illustrative embodiments may be implemented in a data processing system including components in addition to or in place of those illustrated for data processing system 600. Other components shown in FIG. 6 can be varied from the illustrative examples shown.

The different embodiments may be implemented using any hardware device or system capable of executing program code. As one example, the data processing system may include organic components integrated with inorganic components and/or may be comprised entirely of organic components excluding a human being. For example, a storage device may be comprised of an organic semiconductor.

As another example, a storage device in data processing system 600 is any hardware apparatus that may store data. Memory 606, persistent storage 608, and computer readable media 618 are examples of storage devices in a tangible form.

In another example, a bus system may be used to implement communications fabric 602 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 606 or a cache such as found in an interface and memory controller hub that may be present in communications fabric 602.

Figure 7:
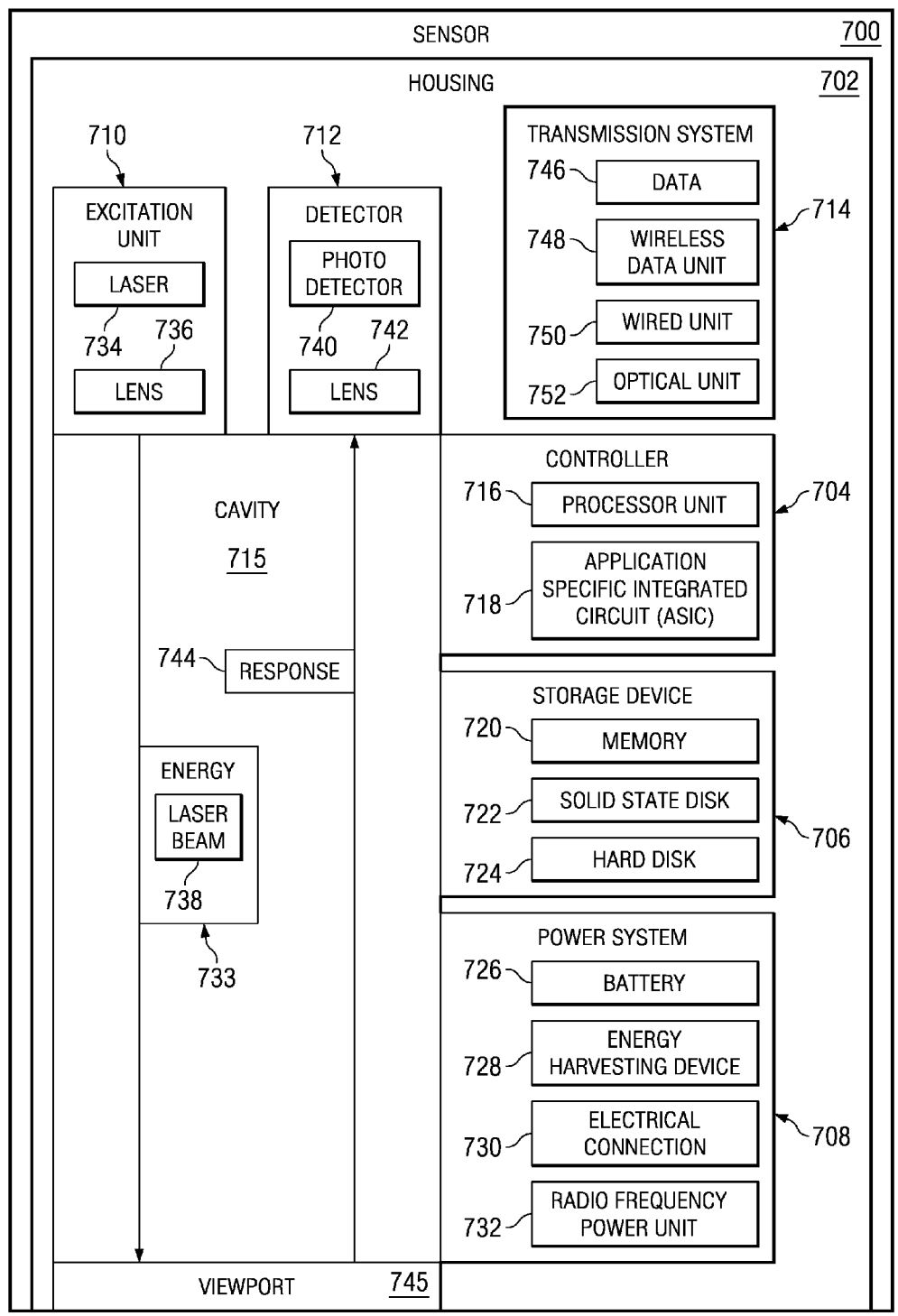
FIG. 7 is a block diagram of a sensor in accordance with an advantageous embodiment.

With reference now to FIG. 7, a block diagram of a sensor is depicted in accordance with an advantageous embodiment. In this example, sensor 700 is an example of one implementation for a sensor within number of sensors 322 in FIG. 3. Sensor 700 may include housing 702, controller 704, storage device 706, power system 708, excitation unit 710, detector 712, and transmission system 714.

Housing 702 may have cavity 715. Cavity 715 may take the form of a hood, shield, vacuum hood, or some other housing that may be capable of shielding the different components of sensor 700 in cavity 715 of housing 702 from unwanted or undesired radiation. Housing 702 may be comprised of aluminum with a coating of flat black paint. In another illustrative example, housing 702 may be comprised of a composite material.

In this example, controller 704 may be implemented in various manners. For example, without limitation, controller 704 may be processor unit 716, application specific integrated circuit (ASIC) 718, or some other suitable type of controller.

In these examples, storage device 706 is capable of storing data that may be gathered when monitoring for corrosion. Storage device 706 may be at least one of memory 720, solid state disk 722, hard disk 724, and/or some other suitable storage device.

Power system 708 provides power to the different components in sensor 700. Power system 708 may be, for example, at least one of battery 726, energy harvesting device 728, electrical connection 730, radio frequency power unit 732, and/or some other suitable power system. Energy harvesting device 728 may take various forms. For example, energy harvesting device 728 may be any device capable of generating energy by exposure to the environment around the device.

In these examples, energy harvesting device 728 may be, for example, a solar cell. In other advantageous embodiments, energy harvesting device 728 may harvest energy from changes in temperature, vibrations, and/or other suitable environmental conditions. Electrical connections 730 may form power system 708 in some advantageous embodiments when sensor 700 is directly connected to a power source. Radio frequency power unit 732 may provide a capability to receive power in a wireless manner from a power source.

Excitation unit 710 is capable of generating energy 733, which may be sent into a location of an object. Excitation unit 710 may cause an excitation of a quantum dot, depending on the state of the quantum dot. In this illustrative example, excitation unit 710 may include laser 734 and lens 736. Lens 736 may direct energy 733 in the form of laser beam 738 when generated by laser 734. For example, lens 736 may be capable of directing laser beam 738 to the surface of an object. Laser 734 may be a gated laser. A gated laser is a laser that may be selectively turned on and off through a mechanism, such as a circuit or other device.

Detector 712 may include photo detector 740 and lens 742. Lens 742 is capable of directing response 744 generated in response to the application of laser beam 738 to quantum dots through viewport 745. Photo detector 740 may be, for example, a gated photo-silicon detector. Of course, detector 740 may include other types of devices in place of, or in addition to, photo detector 740.

Of course, other types of detectors may be used for detector 712. For example, detector 712 may be implemented using a charge injection device (CID) camera, a complementary metal oxide semi conductor (CMOS) camera, an infrared camera, and/or some other suitable type of camera or detector.

Transmission system 714 may transmit data 746 to a computer such as, for example, computer 308 in FIG. 3. Transmission system 714 may transmit data 746 using at least one of wireless data unit 748, wired unit 750, optical unit 752, and/or some other suitable type of transmission device.

Wired unit 750 may be an interface to a network connector or cable. Optical unit 752 may provide a connection to an optical fiber for transmitting data 746. Wireless unit 748 might transmit data 746 without the need for a physical connection to the computer.

Sensor 700 may have various sizes and shapes. For example, housing 702 may have a shape such as, for example, a cube, a cylinder, a hemisphere, or some other suitable shape. The size of sensor 700 may vary depending on the particular location in which sensor 700 is to be placed within an object.

The illustration of sensor 700 in FIG. 7 is not meant to imply physical or architectural limitations to the manner in which sensor 700 may be implemented. In some advantageous embodiments, other components in addition to, or in place of the ones illustrated, may be present. In yet other advantageous embodiments, some components may be omitted.

For example, in some advantageous embodiments, controller 704 may be unnecessary. Instead, sensor 700 may be coupled to a remote controller and/or computer. In yet other advantageous embodiments, additional lasers, in addition to laser 734, may be present in excitation unit 710. These different lasers may generate laser beams similar to laser beam 738. The responses from all of these lasers may be detected by detector 712. In yet other advantageous embodiments, additional detectors may be present.

In still other advantageous embodiments, other types of energy devices may be implemented in excitation unit 710 other than laser 734. For example, excitation unit 710 may be a light-emitting diode, and/or some other device capable of generating a light having a desired beam shape and/or wavelength.

Figure 8:
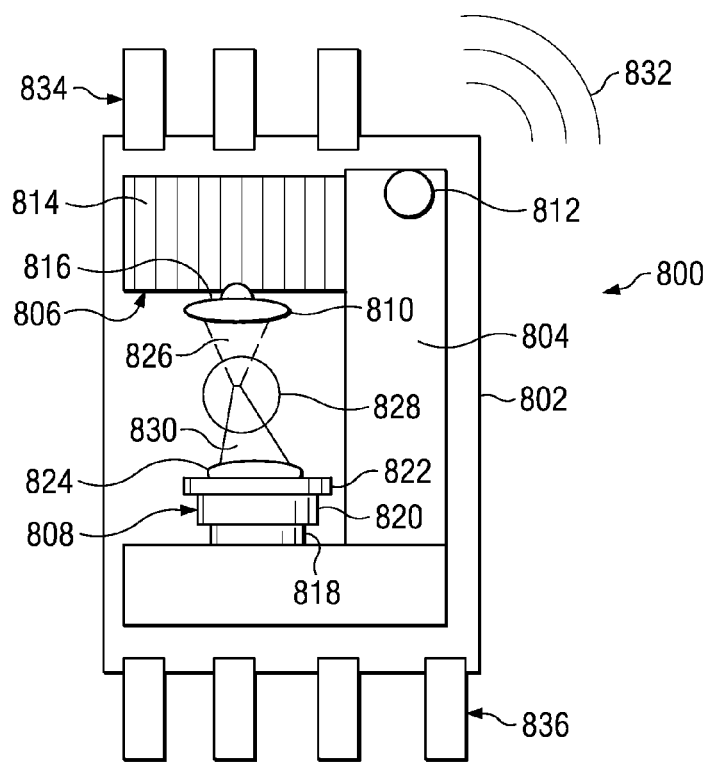
FIG. 8 is a diagram of a sensor in accordance with an advantageous embodiment.

With reference next to FIG. 8, a diagram of a sensor is depicted in accordance with an advantageous embodiment. In this example, sensor 800 is an example of one implementation of sensor 700 in FIG. 7. In this example, housing 802 for sensor 800 may contain controller 804, excitation unit 806, detector 808, and transmitter 812.

Excitation unit 806 may include laser 814 and lens 816. Laser 814 may be a gated laser. In this illustrative example, detector 808 takes the form of a gated photo detector. Detector 808 may have photo detector 818, phosphorous screen 820, micro-channel plate 822, and lens 824.

Laser 814 may generate laser beam 826, which may be directed through viewport 828 onto a surface of an object. When laser 814 is a gated laser, laser 814 may generate laser beam 826 in a manner that laser beam 826 is only emitted periodically and/or non-periodically, rather than continuously. Laser beam 826 may be directed through viewport 828 by lens 816.

Response 830 may be received through viewport 828 by detector 808. Response 830 may pass through lens 824. Micro-channel plate 822 may allow for detection of response 830 without allowing light from laser beam 826 to be directed into photo detector 818.

Micro-channel plate 822 may be a planar component used for detecting particles and/or impinging radiation. Micro-channel plate 822 may be used to intensify response 830. Micro-channel plate 822 may act as a gate that may selectively allow light to pass in a similar fashion to an electronic shutter on a camera. In other words, micro-channel plate 822 may control exposure of detector 808 to light.

Phosphorous screen 820 may convert electrons in the light back into photons. This conversion may allow response 830 to be imaged and/or detected using photo detector 818. In these examples, photo detector 818 may be, for example, a photo diode, an image sensor, and/or some other suitable detector.

This gating used in sensor 800 may eliminate a need for a narrow band pass optical filter. The use of a narrow band pass optical filter may be undesirable in some implementations, because this type of filter may reduce the intensity detected for response 830. For example, laser beam 826 may be emitted from laser 814 when micro-channel plate 822 is closed or does not allow light to pass. After laser beam 826 ceases to be emitted from laser 814, micro-channel plate 822 may open and/or allow response 830 to pass through to photo detector 818.

Controller 804 may control the operation of excitation unit 806 and detector 808 in sensor 800. Further, controller 804 may process response 830 as detected by photo detector 818. Controller 804 may generate data which may be transmitted by transmitter 812 to a computer for processing. In these examples, transmitter 812 may be a wireless transmitter that uses wireless transmission 832 to transmit the data.

Electrical connectors 834 and 836 may provide an electrical connection for sensor 800. These connectors may be connected to a power source to provide power for the different components in sensor 800.

The illustration of sensor 800 in FIG. 8 is not meant to imply physical or architectural limitations to the manner in which other sensors may be implemented. For example, in other advantageous embodiments, multiple photo sensors may be present within housing 802. In yet other advantageous embodiments, housing 802 may have different shapes. For example, the housing may have a cube shape with a side having a length of around one centimeter, around two centimeters, around three centimeters, or some other suitable length. Further, in other advantageous embodiments, housing 802 may have some other suitable shape, depending on the particular implementation.

Figure 9:
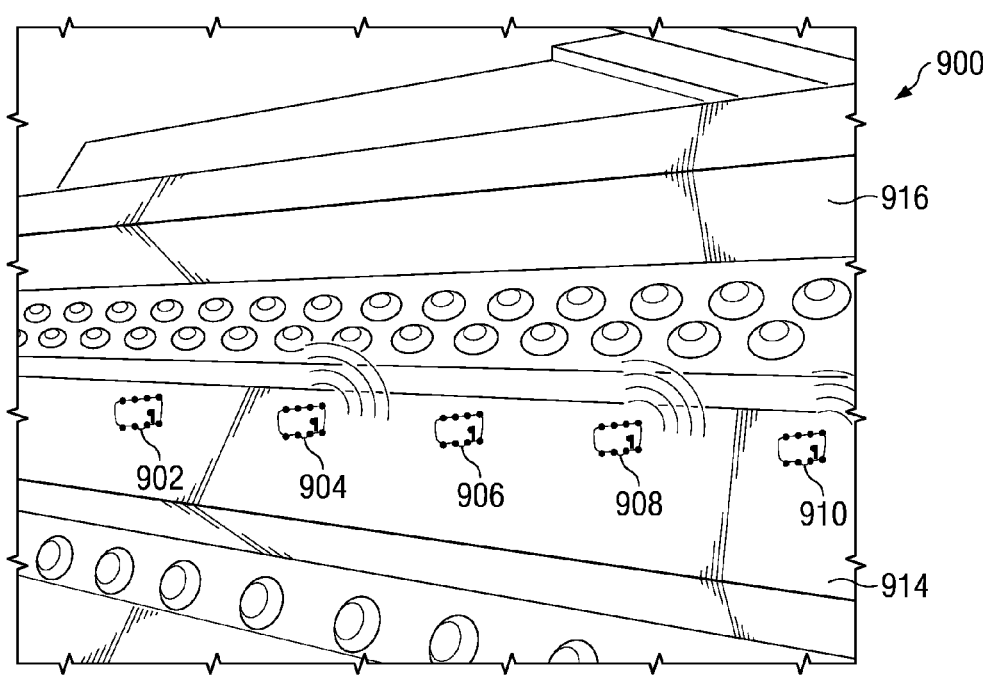
FIG. 9 is a diagram illustrating an association of sensors with an object in accordance with an advantageous embodiment.

Turning now to FIG. 9, a diagram illustrating an association of sensors with an object is depicted in accordance with an advantageous embodiment. In this example, a portion of object 900 is depicted with sensors 902, 904, 906, 908, and 910. Object 900 is an example of an object, such as object 310 in FIG. 3. In particular, object 900 may be an aircraft such as, for example, aircraft 200 in FIG. 2. Sensors 902, 904, 906, 908, and 910 may be implemented using a sensor such as, for example, without limitation, sensor 800 in FIG. 8.

Sensors 902, 904, 906, 908, and 910 are attached to surface 914 of object 900 for hidden structure 916 in object 900. These sensors may be attached to surface 914 of object 900 during the manufacturing of object 900. In other advantageous embodiments, these sensors may be attached to surface 914 during maintenance and/or refurbishing of object 900.

By attaching sensors 902, 904, 906, 908, and 910 to surface 914, corrosion for surface 914 may be monitored without requiring disassembly of object 900 to reach hidden structure 916. Further, if coatings or other layers are present on surface 914, removal of those layers and/or coatings may be unnecessary.

Figure 10:
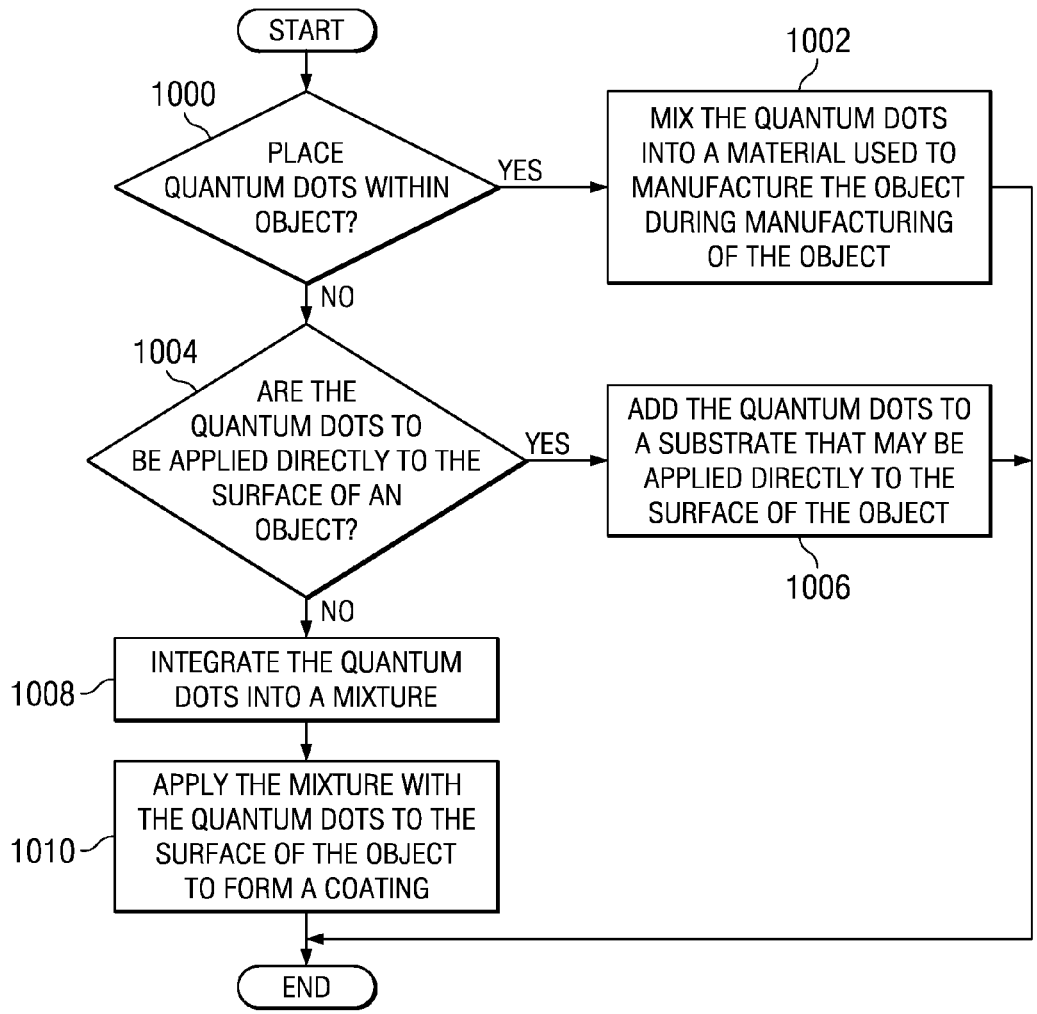
FIG. 10 is a flowchart of a process for associating quantum dots with an object in accordance with an advantageous embodiment.

Turning now to FIG. 10, a flowchart of a process for associating quantum dots with an object is depicted in accordance with an advantageous embodiment. The process illustrated in FIG. 10 may be used to associate quantum dots, such as quantum dots 328 in FIG. 3 for use in monitoring an object, such as object 310 in FIG. 3. This process may be performed during various steps, operations, and/or phases in manufacturing, performing maintenance, refurbishing, and/or otherwise modifying an object. For example, the process illustrated in FIG. 10 may be implemented during component and subassembly manufacturing 106, system integration 108, and/or maintenance and service 114 in FIG. 1. In other words, this process may be used to associate quantum dots with locations in an object.

The process begins by determining whether to place quantum dots within the object (operation 1000). If quantum dots are to be placed into the object, the quantum dots may be mixed into a material used to manufacture the object during manufacturing of the object (operation 1002), with the process terminating thereafter. In operation 1002, quantum dots may be placed into a resin and/or other composite material used for an object that may employ composite parts and/or structures.

With reference again to operation 1000, if quantum dots are not to be placed into the object, a determination is made as to whether quantum dots are to be applied directly to the surface of an object (operation 1004). If quantum dots are to be applied directly to the surface of the object, the quantum dots are added to a substrate that may be applied directly to the surface of the object (operation 1006), with the process terminating thereafter. In operation 1006, the quantum dots may be mixed into a solution that may cause the quantum dots to adhere to, bond, and/or otherwise be secured to the surface of the object.

With reference again to operation 1004, if the quantum dots are not to be applied directly to the surface of the object, the process integrates the quantum dots into a mixture (operation 1008). This mixture may be, for example, a primer, paint, sealant, or some other suitable mixture. The mixture with the quantum dots is then applied to the surface of the object to form a coating (operation 1010), with the process terminating thereafter.

Figure 11:
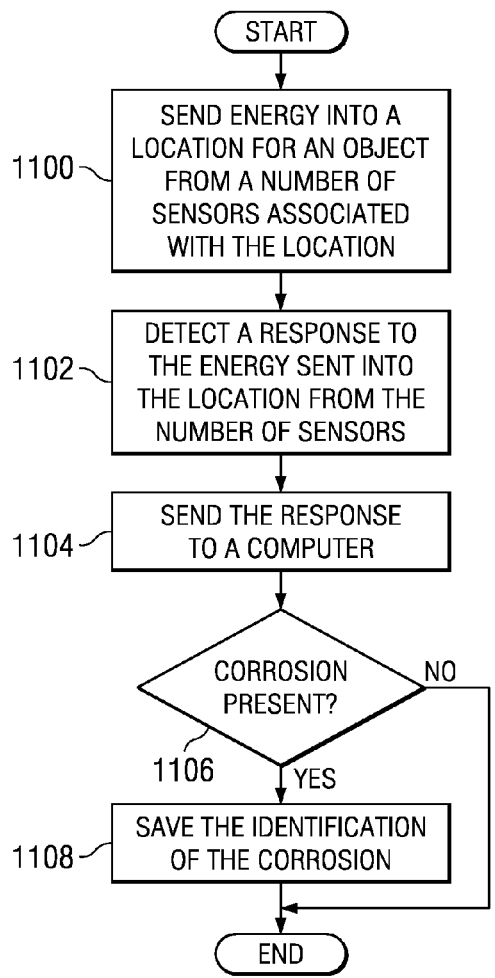
FIG. 11 is a flowchart of a process for detecting corrosion in accordance with an advantageous embodiment.

Turning to FIG. 11, a flowchart of a process for detecting corrosion is depicted in accordance with an advantageous embodiment. The process illustrated in FIG. 11 is an example of a process that may be implemented to monitor an object for corrosion. The process illustrated in this figure may be implemented in a health monitoring system such as, for example, without limitation, health monitoring system 302 in FIG. 3.

The process begins by sending energy into a location for an object from a number of sensors associated with the location (operation 1100). In sending the energy into the location, each of the number of sensors may individually send a portion of the energy. For example, a laser beam may be sent from each of the number of sensors associated with a surface of the object into the location for the object to form a number of laser beams. In some advantageous embodiments, only some of the number of sensors may be used, depending on the particular implementation.

This location is associated with quantum dots. The quantum dots may be associated with the location in a number of different ways. For example, the quantum dots may be present in the substrate of the object. This substrate may be a coating covering the surface of the object. In some advantageous embodiments, this substrate may be a portion of the object itself.

In yet other advantageous embodiments, the quantum dots may be attached and/or bonded to a surface of the object at the location to associate the quantum dots with the location. These quantum dots may be capable of emitting a response that can be analyzed to determine whether corrosion has occurred in the location for the object.

The process then detects a response to the energy sent into the location from the number of sensors (operation 1102). The process then sends the response to a computer (operation 1104). The response detected may be light generated by the quantum dots. This response may include data detected by the number of sensors. In other words, each sensor may detect light that may be generated in response to sending the energy into the location. Each of these sensors may then generate data that forms the response.

A determination is then made using the computer as to whether corrosion is present based on the response (operation 1106). If corrosion is present, the identification of the corrosion is saved (operation 1108). Otherwise, the process terminates.

Figure 12:
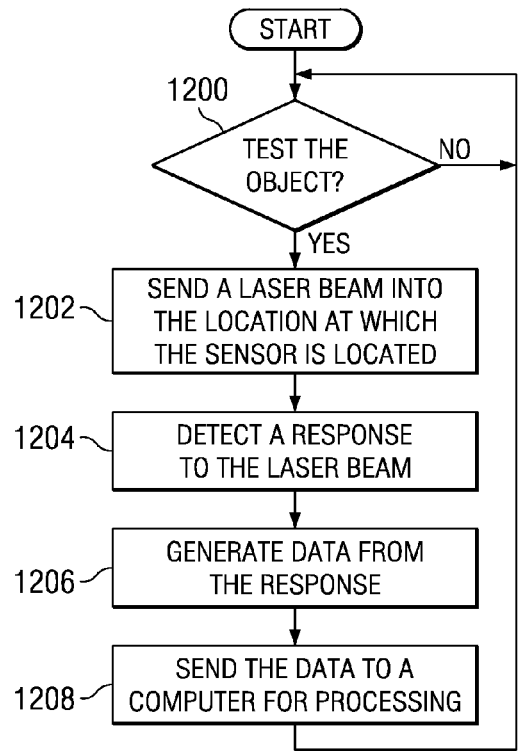
FIG. 12 is a flowchart of a process for obtaining data from an object with quantum dots in accordance with an advantageous embodiment.

With reference now to FIG. 12, a flowchart of a process for obtaining data from an object with quantum dots is depicted in accordance with an advantageous embodiment. The process illustrated in FIG. 12 may be implemented in an environment, such as monitoring environment 300 in FIG. 3. In particular, this process may be implemented in sensor system 306 in health monitoring system 302 in FIG. 3.

The process begins by determining whether to test the object (operation 1200). This determination may be made at a sensor. The determination may be based on an event that may be periodic or non-periodic. For example, the event may be a signal or a command received from a computer. In other advantageous embodiments, the event may be the expiration of a period of time or a timer. Further, other events may be used. For example, the sensor may detect a change in the environment, such as a change in temperature, moisture, and/or other environmental parameter.

If the object is to be tested, a laser beam is sent into the location at which the sensor is located (operation 1202). The process then detects a response to the laser beam (operation 1204). Data is generated from the response (operation 1206). Operation 1206 may include placing the data into a form for transmission to a computer. In some advantageous embodiments, this operation may also include some pre-processing of the response. For example, data associating the location of the sensor with the data may be included. Some initial processing, such as identifying an intensity, a wavelength, and/or other suitable information also may be performed.

Further, other environmental information may be collected and included in this process. This environmental information also may include, for example, temperature, moisture, and/or other suitable information.

The process then sends the data to a computer for processing (operation 1208), with the process then returning to operation 1200. With reference again to operation 1200. If testing is not to be performed, the process continues to return to operation 1200 until testing is needed.

Figure 13:
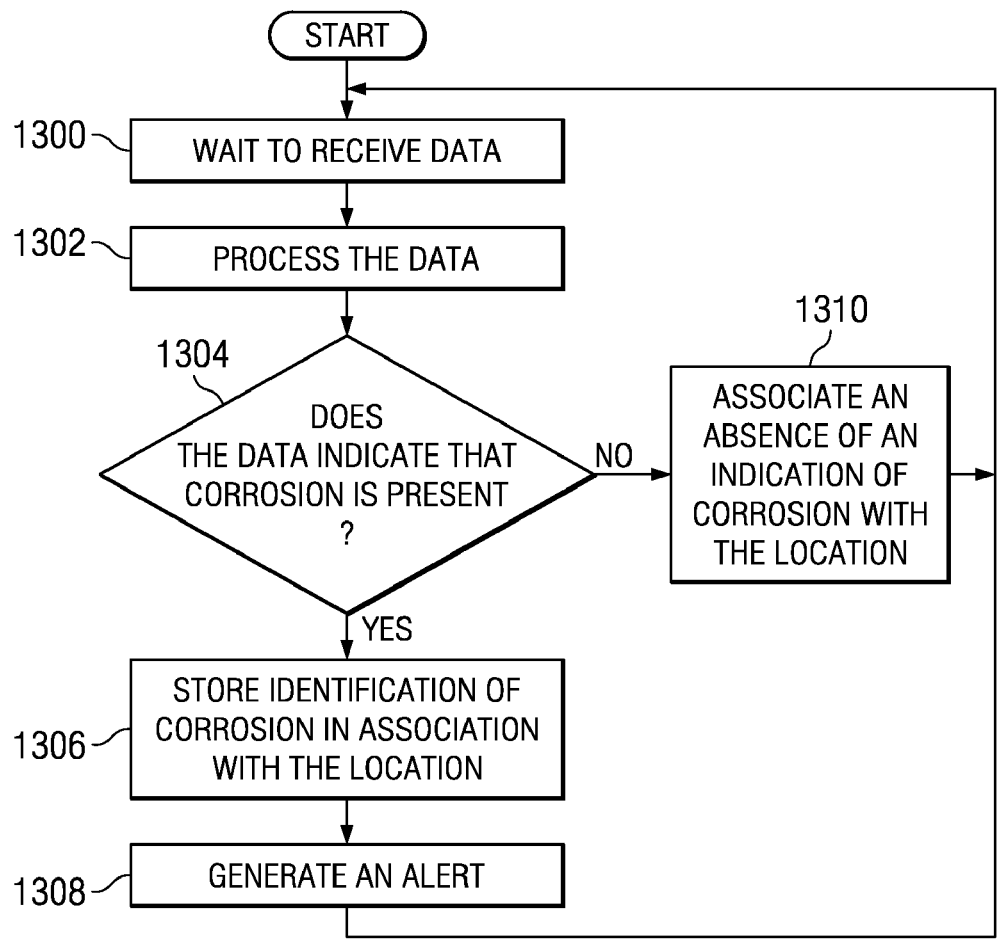
FIG. 13 is a flowchart of a process for determining whether corrosion has occurred in accordance with an advantageous embodiment.

With reference now to FIG. 13, a flowchart of a process for determining whether corrosion has occurred is depicted in accordance with an advantageous embodiment. The process in FIG. 13 may be implemented in monitoring environment 300 in FIG. 3. More specifically, program 354 executing on computer 308 in health monitoring system 302 in FIG. 3 is an example of a software component that may implement this process.

The process begins by waiting to receive data from sensors (operation 1300). When data is received, the process then processes the data (operation 1302). In processing the data, the process may identify a location, strength, intensity, and/or wavelength for the data received. Operation 1302 also may identify other types of information based on the data received. For example, other information may be included, such as environmental information.

A determination is then made as to whether the data indicates that corrosion is present (operation 1304). This determination may be made by identifying the expected wavelength for the quantum dots. In other advantageous embodiments, the determination may be made by determining whether a particular wavelength is present.

In these illustrative examples, this determination may compare the wavelength in the data to an expected wavelength that is present when a quantum dot has been exposed to free hydrogen+. Such a change may indicate that corrosion may be present. In these illustrative examples, the amount of corrosion may be detected based on the intensity of the light. As more corrosion is present, more quantum dots generate light in these examples.

If corrosion is identified as being present, this identification is stored in association with the location (operation 1306). The process also may generate an alert (operation 1308). This alert may be presented on a display device and/or sent in an email, a text message, through a voice prompt, or some other suitable process or device for generating and/or delivering alerts. The process then returns to operation 1300 to wait to receive data from a sensor. With reference again to operation 1304, if the data does not indicate that corrosion is present, the process then associates an absence of an indication of corrosion with the location (operation 1310).

The flowcharts and block diagrams in the different depicted embodiments illustrate the architecture, functionality, and operation of some possible implementations of apparatus and methods in different advantageous embodiments. In this regard, each block in the flowcharts or block diagrams may represent a module, segment, function, and/or a portion of an operation or step. In some alternative implementations, the function or functions noted in the blocks may occur out of the order noted in the figures. For example, in some cases, two blocks shown in succession may be executed substantially concurrently, or the blocks may sometimes be executed in the reverse order, depending upon the functionality involved.

Thus, the different advantageous embodiments provide a capability to detect corrosion in a nondestructive manner. The different advantageous embodiments may provide a capability to monitor one or more locations on an object for corrosion through the use of a health monitoring system. With some of the advantageous embodiments, the need for visually inspecting an aircraft for corrosion may be reduced and/or avoided.

Further, with the different advantageous embodiments, a removal of coatings for inspection also may be reduced and/or avoided. Disassembly of components or structures in an object also may be reduced in frequency and/or avoided using the health monitoring system described in the different advantageous embodiments. Further, the different advantageous embodiments may provide a capability to monitor an object without requiring the object to be removed from use for maintenance and/or inspection.

The different advantageous embodiments can take the form of an entirely hardware embodiment, an entirely software embodiment, or an embodiment containing both hardware and software elements. Some embodiments are implemented in software, which includes, but is not limited to, forms such as, for example, firmware, resident software, and microcode.

Furthermore, the different embodiments can take the form of a computer program product accessible from a computer usable or computer readable medium providing program code for use by, or in connection with, a computer or any device or system that executes instructions. For the purposes of this disclosure, a computer usable or computer readable medium can generally be any tangible apparatus that can contain, store, communicate, propagate, or transport the program for use by, or in connection with, the instruction execution system, apparatus, or device.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters and are just a few of the currently available types of communications adapters.

The description of the different advantageous embodiments has been presented for purposes of illustration and description, and it is not intended to be exhaustive or limited to the embodiments in the form disclosed. Many modifications and variations will be apparent to those of ordinary skill in the art. Although the different advantageous embodiments have been described with respect to aircraft, other advantageous embodiments may be applied to other types of objects.

For example, without limitation, other advantageous embodiments may be applied to a mobile platform, a stationary platform, a land-based structure, an aquatic-based structure, a space-based structure, and/or some other suitable object.

More specifically, the different advantageous embodiments may be applied to, for example, without limitation, a submarine, a bus, a personnel carrier, a tank, a train, an automobile, a spacecraft, a space station, a satellite, a surface ship, a power plant, a dam, a manufacturing facility, a building, a cargo bay, a door sill, a landing gear bay, an insulation blank, a bilge, a seat track, a leading edge of a wing, a trailing edge of a wing, a trailing edge of a stabilizer, a fuel tank, and/or some other suitable object.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   a number of sensors capable of being associated with a location of an object having quantum dots, wherein the number of sensors is capable of sending energy into the location in which the energy is capable of causing a response from the quantum dots, wherein the quantum dots have been exposed to hydrogen+ and wherein the number of sensors is capable of detecting the response; and
   a computer coupled to the number of sensors and capable of determining whether corrosion is present in the location using the response detected by the number of sensors.

2. The apparatus of claim 1 further comprising:
   a network coupling the computer to the number of sensors.

3. The apparatus of claim 2, wherein the network has a number of connections selected from at least one of a wired connection, an optical connection, and a wireless connection.

4. The apparatus of claim 2, wherein the number of sensors, the computer, and the network form a health monitoring system.

5. The apparatus of claim 1, wherein a sensor in the number of sensors comprises:
   a housing;
   a laser attached to the housing and capable of transmitting a laser beam into the location;
   a detector attached to the housing and capable of detecting the response to the laser beam generated by the quantum dots when the quantum dots have been exposed to hydrogen+; and
   a transmitter capable of sending the response to the computer over a network.

6. The apparatus of claim 5 further comprising:
   a controller capable of causing the laser to transmit the laser beam.

7. The apparatus of claim 6, wherein the controller causes the laser to transmit the laser beam in response to at least one of a signal from the computer, an expiration of a period of time, and an event.

8. The apparatus of claim 1 further comprising:
   a power system.

9. The apparatus of claim 8, wherein the power system comprises at least one of a battery, a power harvesting device, and a radio frequency power unit.

10. The apparatus of claim 1, wherein a sensor in the number of sensors comprises:
    a housing;
    a laser attached to the housing and capable of transmitting a laser beam into the location;
    a detector attached to the housing and capable of detecting the response to the laser beam generated by the quantum dots when the quantum dots have been exposed to hydrogen+;
    a transmitter capable of sending the response to the computer over a network;
    a controller capable of causing the laser to transmit the laser beam, wherein the controller causes the laser to transmit the laser beam in response to at least one of a signal from the computer, an expiration of a period of time, and an event; and a power system comprised of at least one of a battery, a power harvesting device, and a radio frequency power unit.

11. The apparatus of claim 1, wherein the object is selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, a building, a cargo bay, a door sill, a landing gear bay, an insulation blank, a bilge, a seat track, a leading edge of a wing, a trailing edge of a wing, a trailing edge of a stabilizer, and a fuel tank.

12. A sensor comprising:
a housing capable of being associated with a surface of an object having quantum dots;
a laser attached to the housing and capable of transmitting a laser beam onto the surface of the object;
a detector attached to the housing and capable of detecting a response to the laser beam generated by the quantum dots when the quantum dots have been exposed to hydrogen+; and
a transmitter capable of sending the response to a computer over a network.

13. The sensor of claim 12 further comprising:
a controller capable of causing the laser to transmit the laser beam.

14. The sensor of claim 13, wherein the controller is capable of processing the response to form a processed response and sending the processed response to the computer.

15. The sensor of claim 12 further comprising:
a power system.

16. The sensor of claim 15, wherein the power system comprises at least one of a battery, a power harvesting device, and a radio frequency power unit.

17. The sensor of claim 12, wherein the laser is a gated laser.

18. The sensor of claim 12, wherein the detector is a gated photo-silicon detector.

19. The sensor of claim 12 further comprising:
a lens system capable of directing the laser beam to the surface and directing the response to the sensor.

20. The sensor of claim 12 further comprising:
a phosphorous screen capable of converting electrons in the response into photons.

21. A method for detecting corrosion, the method comprising:
sending energy into a location for an object from a number of sensors associated with the location, wherein the location is associated with quantum dots;
detecting a response to the energy sent into the location from the number of sensors when the quantum dots have been exposed to hydrogen+; and
determining whether the corrosion is present based on the response.

22. The method of claim 21, wherein the sending step comprises:
sending a laser beam from each of the number of sensors associated with a surface of the object into the location for the object to form a number of laser beams.

23. The method of claim 22, wherein the detecting step comprises:
receiving the response to the laser beam at each of the number of sensors to form a number of responses.

24. The method of claim 21 further comprising:
sending the response to a computer, wherein the computer determines whether the corrosion is present.

25. The method of claim 21, wherein each of the number of sensors sends a value identifying at least one of an intensity and a wavelength of the response detected by the each of the number of sensors.

26. The method of claim 21, wherein the quantum dots are located in a substrate for the object.

27. The method of claim 26, wherein the substrate is selected from one of a coating applied to the object and the object.

28. The method of claim 21, wherein the object is selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, a building, a cargo bay, a door sill, a landing gear bay, an insulation blank, a bilge, a seat track, a leading edge of a wing, a trailing edge of a wing, a trailing edge of a stabilizer, and a fuel tank.

* * * * *